(12) United States Patent
Spasovski (10) Patent No.: US 9,675,245 B2
(45) Date of Patent: Jun. 13, 2017

(54) METHOD AND DEVICE FOR DETERMINING THE EYE TORSION

(75) Inventor: Saso Spasovski, Berlin (DE)

(73) Assignee: Chronos Vision GmbH, Berlin (DE)

( * ) Notice: Subject to any disclaimer, the term of this patent is extended or adjusted under 35 U.S.C. 154(b) by 607 days.

(21) Appl. No.: 13/809,954

(22) PCT Filed: Jul. 23, 2011

(86) PCT No.: PCT/DE2011/001514
§ 371 (c)(1),
(2), (4) Date: Mar. 11, 2013

(87) PCT Pub. No.: WO2012/013186
PCT Pub. Date: Feb. 2, 2012

(65) Prior Publication Data
US 2013/0162947 A1  Jun. 27, 2013

(30) Foreign Application Priority Data
Jul. 24, 2010 (DE) .................. 10 2010 032 193

(51) Int. Cl.
*A61B 3/113* (2006.01)
*A61B 3/14* (2006.01)
(Continued)

(52) U.S. Cl.
CPC ............ *A61B 3/113* (2013.01); *A61B 3/0025* (2013.01); *A61B 3/14* (2013.01); *G06T 7/0016* (2013.01);
(Continued)

(58) Field of Classification Search
CPC ......... A61B 3/0025; A61B 3/113; A61B 3/14; G06T 2207/30101; G06T 2207/30104;
(Continued)

(56) References Cited

U.S. PATENT DOCUMENTS 6,120,461 A * 9/2000 Smyth ........................ 600/558
2003/0223037 A1* 12/2003 Chernyak ............ A61B 3/1015
351/209
(Continued)

FOREIGN PATENT DOCUMENTS

DE   102006002001 A1   7/2007
JP      11-096372 A     4/1999

OTHER PUBLICATIONS

Lopez et al., Torsional optokinetic nystagmus after unilateral vestibular loss: asymmetry and compensation, 2005, Brain, 128, 1511-1524.*
Urano et al., "Fast and Robust Rotation-invariant Search by Using Orientation Code Difference Histogram", Proceedings of SPIE vol. 6051, 605101, (2005) 0277-786x/05/$15 doi: 10.1117/12.645483.
(Continued)

*Primary Examiner* — Huy K Mai
*Assistant Examiner* — Gary O'Neill
(74) *Attorney, Agent, or Firm* — Hauptman Ham, LLP (57) ABSTRACT

The invention relates to a device for determining eye torsion, comprising a camera and an image processing unit, which is designed to carry out a method for determining eye torsion. In the method, at least two images of an eye are recorded and image data are produced from said images, and at least one characteristic feature of the eye is identified from the image data, for example a blood vessel. Direction histograms of the feature in both images are produced and compared with each other. The angle of the torsion of the eye is determined from the shift of the directions in the direction histograms.

15 Claims, 6 Drawing Sheets

(51) Int. Cl.
  *A61B 3/00* (2006.01)
  *G06T 7/00* (2017.01)
  *G06T 7/73* (2017.01)
(52) U.S. Cl.
  CPC ...... *G06T 7/74* (2017.01); *G06T 2207/30041* (2013.01); *G06T 2207/30101* (2013.01)
(58) Field of Classification Search
  CPC ... G06T 7/0016; G06T 7/0044; G06T 7/0046; G06T 7/0048
  USPC ....... 351/206, 209, 246; 396/18, 51; 348/78; 382/169–172
  See application file for complete search history.

(56) References Cited

U.S. PATENT DOCUMENTS

| | | | |
|---|---|---|---|
| 2005/0024586 A1* | 2/2005 | Teiwes | A61B 3/113 351/209 |
| 2005/0213818 A1* | 9/2005 | Suzuki et al. | 382/190 |
| 2007/0171369 A1 | 7/2007 | Grundig | |

OTHER PUBLICATIONS

Kim, Soo Chan et al., "A new method for accurate and fast measurement of 3D eye movements", Medical Engineering Physics, 2006, pp. 82-89.

Paliulis, E. et al., "Determination of Eye Torsion by Videooculography Including Cornea Optics", Electronics and Electrical Engineering, 2006, pp. 83-86.

Zhu, Danjie et al., "Robust and real-time torsional eye position calculation using a template-matching technique", Computer Methods and Programs in Biomedicine, 2004, pp. 201-209.

Urano, Takahiro et al., "Fast and Robust Rotation-invariant Search by Using Orientation Code Difference Histogram", Proc. of Spie, 2005, vol. 6051, pp. 605101-1-605101-12.

Miranda Pav et al., "TSD: a shape descriptor based on a distribution of tensor scale local orientation", 18th Brazilian Symposium on Computer Graphics and Image Processing IEEE Comput. Soc., 2005, pp. 1-8.

Zhu, Qiang et al., "A New Approach for Rotated Face Detection", 2001, pp. 537-539.

Written Opinion issued in PCT/DE2011/001514 on Jan. 29, 2013.

International Search Report mailed May 2, 2012, in corresponding International Application No. PCT/DE2011/001514.

* cited by examiner

METHOD AND DEVICE FOR DETERMINING THE EYE TORSION

RELATED APPLICATIONS

The present application is a National Phase of International Application Number PCT/DE2011/001514, filed Jul. 23, 2011, and claims priority from German Application Number 102010032193.1, filed Jul. 24, 2010.

The invention relates to a method and a device for determining the eye torsion.

BACKGROUND OF THE INVENTION

In the field of medical engineering as well as for equilibrium studies, it is important to determine the torsion of the human eye, i.e. the rotation of the eye around the viewing direction (z-axis). In medical engineering, for example for the insertion of toric intraocular lenses, the rotation of the eye must be known exactly in order to ensure the exact adjustment of the lens in relation to the eye. But also for a laser treatment of the eye or its preparation, the knowledge of torsional movements of the eye leads to a more precise result. Further possible fields of application include neuroscience research or investigations of the effect of images or visual stimulations on the human being, for example in the field of advertisement and communications.

Document DE102006002001 describes a method for determining the spatial relationship of an eye with reference to a camera device, in which a model of the eye is constructed and a reference relation of the eye model is determined by using a reference image of the eye. Thereafter position and rotation coordinates are determined by adapting the eye model to a current image of the eye. The eye model comprises texture information which is stored as a feature template map. Features of the feature template map are blood vessels, iris characteristics, limb, limb centre, pupil centre, pupil edge and artificial markers. However, the creation and adaptation of eye models is complex and requires high processing power and corresponding computation time.

When determining the torsion from images of the eye which are taken by a camera, there exists particularly the problem that in addition to the rotation, the image regions may have different sizes and may be out of alignment. This complicates the detection of corresponding image regions.

SUMMARY OF THE INVENTION

It is the object of the present invention to provide a method with which the torsion of the eye can be determined quickly and precisely. Furthermore a corresponding device for determining the eye torsion shall be created.

The object is achieved by the method for determining the eye torsion according to claim 1, by the device for determining the eye torsion according to claim 8, and by the computer program according to claim 10. Further advantageous features and details will become apparent from the dependent claims, the description and the drawings.

The basic idea of the determination of the torsion of the eye according to the invention is to identify corresponding image regions in different images, and to determine from their relative position the rotation or torsion, wherein a histogram e.g. of gradient- or tangential directions of a feature is used for determining the torsion. If the image is rotated, the shape of the histogram remains the same. It appears only a displacement or shift on the direction axis of the histogram. The angle of the torsion is determined from the amount of the shift.

According to the method of the invention, at least two images of the eye are captured and image data is generated thereof, in which at least one characteristic feature is identified. Thereafter a direction histogram of the feature of the eye is produced in both images, and the direction histograms of the feature in both images are compared to each other. The angle of the torsion of the eye is determined from the shift or displacement of the directions in the direction histograms.

The invention allows very quick and accurate measurements of eye torsions. Here, the image regions or sections used for determining the torsion can have different sizes and can be displaced relative to each other.

The direction histogram is in particular a histogram of the gradient- or tangential directions of the feature.

It is particularly advantageous to use a blood vessel or a group of blood vessels as a feature or object for the creation of histograms of directions. The direction histograms of the blood vessels have scaling and translation invariant properties, i.e. they keep a constant shape independent from their size and position. However, with a rotation or twist, the histogram is shifted along the axis of direction, and the angle of the torsion can be determined therefrom. Due to their geometrical structure, colour composition and characteristic colour gradients along or perpendicular to the direction of the blood vessels, blood vessels can be identified in the image particularly quickly and reliably. Thereby detailed direction histograms can be created safely, which increases the reliability and the accuracy of the measurement.

But it is also possible to choose other features or objects which are suitable for the determination of the torsion and which have corresponding properties, such as characteristic patterns in the iris. Advantageously, characteristic structures such as blood vessels of the fundus of the eye or of the sclera are selected as characteristic features. Furthermore, artificially applied marks on the sclera and/or the cornea can be chosen as characteristic features.

As an optional embodiment of the method, a total or overall direction histogram of a plurality of blood vessels is calculated in both images respectively, and from their displacement the torsion angle of the eye is determined. Instead of limiting the observation of the histograms to single features or attributes, total direction histograms of all blood vessels or of particularly prominent blood vessels of both images can be calculated. If the distribution of the directions of gradients is sufficiently characteristic, a displacement of the histograms and thus also the angle of torsion can be determined.

As an alternative or supplement, every image can also be divided into subareas or regions, and in each region a direction histogram can be computed and used for comparison. That is, the image can e.g. be divided into N subareas which may partially overlap. Then, a histogram of oriented gradients can be calculated separately in every subarea.

Advantageously the shape of the histograms is compared, where the displacement on the direction axis of the histogram is determined for histograms of equal shapes. If there are few or no similarities, it is probably not the same feature.

The device for determining the eye torsion according to the invention comprises a camera device for capturing at least two images of the eye and for generating image data, an image processing unit for identifying at least one characteristic feature from the image data and for creating a direction histogram of the feature in both images, where the image processing unit is configured for comparing the direction histograms of the features in both images and determines from a shift of the directions in the direction histograms the angle of the eye torsion.

The image processing unit is in particular designed to carry out the method and has corresponding features.

According to an embodiment of the invention, a computer program and a computer unit are provided, which are designed for carrying out the method according to the invention along with an image processing unit connected to a camera device.

Features and details of the invention, which are described in connection with the method, also apply to the corresponding device of the invention and vice versa.

DESCRIPTION OF PREFERRED EXEMPLARY EMBODIMENTS

In the following text, the invention will be described closer and more in detail on the basis of drawings. Here.

Figure 1:
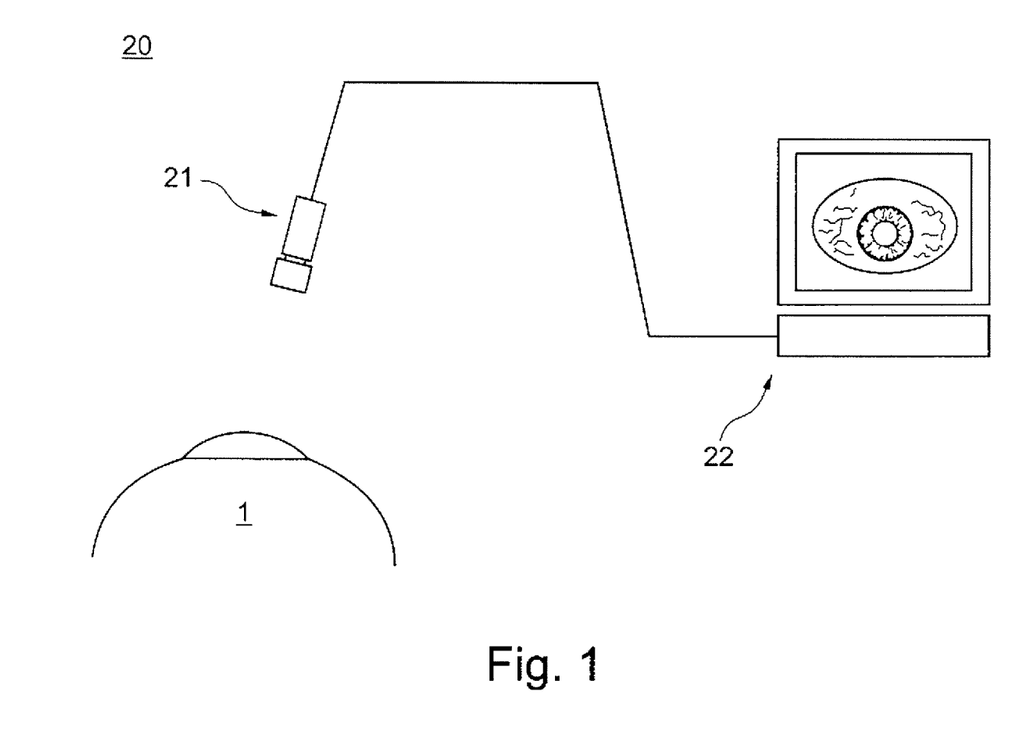
FIG. 1 shows an example of a device for determining the torsion of an eye.

FIG. 1 schematically shows an example of a device 20 for determining the torsion of an eye 1. Here, a camera 21 is used to capture images of the eye 1. The camera 21 is electrically connected to an image processing unit 22 and transmits the image data of the captured images to the image processing unit 22, which determines the torsion angle of the eye 1 as described below.

Figure 2A:
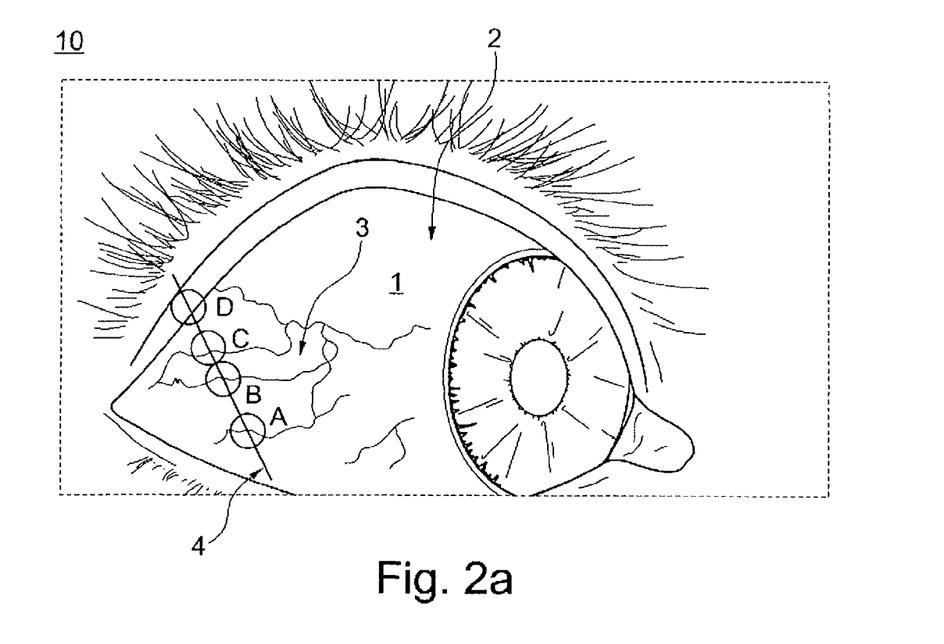
FIGS. 2a and 2b show an image of an eye captured by a camera and a corresponding colour distribution along a line in the image.

FIG. 2a shows an image 10 of the eye 1 taken by the camera 21. In the area of the sclera 2 blood vessels 3 are arranged, which serve to supply the sclera 2 and the cornea. The blood vessels 3 have different directions and form a branched system or network, which substantially extends over the entire sclera 2. By means of the image processing unit 22 (see FIG. 1) an extraction of the blood vessels 3 from the captured image 10 is carried out. As an example, the extraction along a line 4 is described below.

Figure 2B:
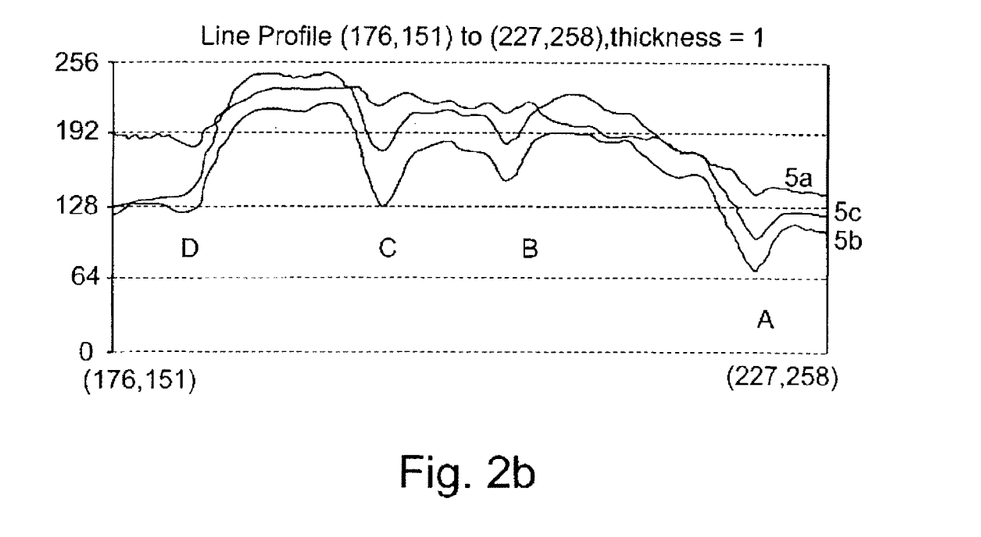

FIG. 2b shows the distribution of colours in image 10 along the line 4. Here, the intensities of the colours red, green and blue (R, G, B) in the curves 5a (=R), 5b (=G) and 5c (=B) are shown. Based on the intensities, the blood vessels and their characteristics are determined. In the curves 5b, 5c local minima occur at the locations A, B, C, while the curve 5a hardly changes or changes in a relatively small amount at these locations. That means that at these points in image 10, intensity minima for green and blue are present, while red remains essentially unchanged. This is a criterion for the detection of the blood vessels 3 in image 10.

In this way, the entire image 10 is analysed for the blood vessels 3. But it is also possible to analyse only one or more portions of the image 10, or to determine or to analyse only the blood vessels having the highest amounts of intensities.

In addition, also other conditions for the presence of blood vessels can be examined and used for the extraction, for example a high amount of white in the vicinity of the blood vessel, a small red gradient along the blood vessel, and a big red gradient perpendicular thereto.

Figure 3:
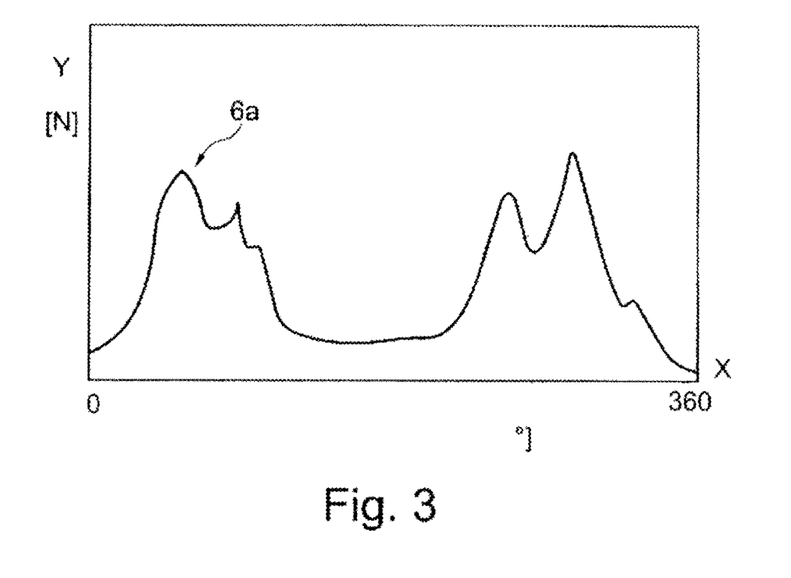
FIG. 3 shows schematically a histogram of oriented gradients of a blood vessel.

FIG. 3 schematically shows a histogram of oriented gradients 6a of a blood vessel 3, which is for example extracted from an image of the eye 1. The creation of histograms of oriented gradients is generally known in the field of image processing, so it will not be explained in more detail here. The histogram of oriented gradients 6a shows the frequencies of occurrence of the directions of the gradient respectively the normal direction of the blood vessel 3 extracted by image processing. Here, the direction of gradients is shown on the axis of direction respectively the x-axis, while the relative frequency of occurrence N of the direction of gradients is shown on the y-axis.

Figure 4:
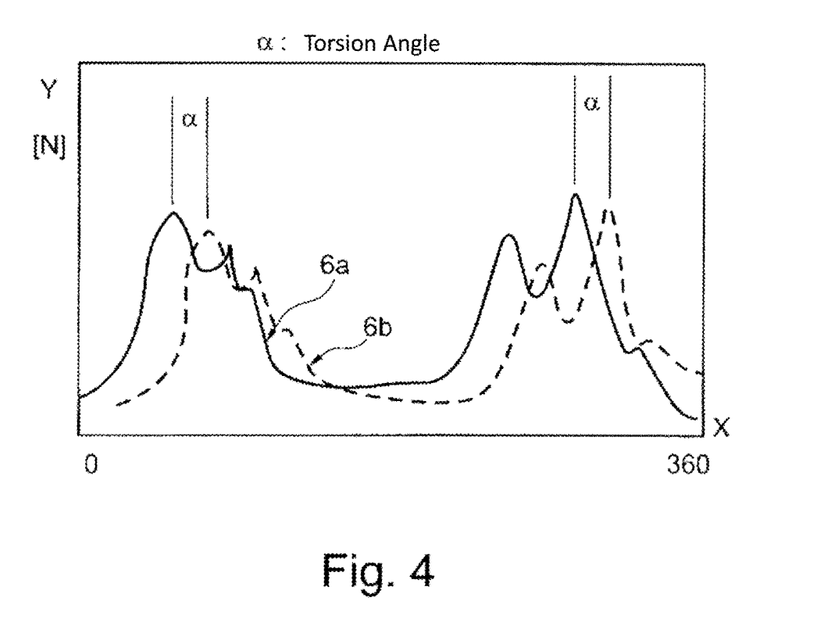
FIG. 4 shows two histograms of oriented gradients of a blood vessel which are displaced relative to each other, and which are created from two images of the eye.

FIG. 4 schematically shows the histogram of oriented gradients 6a, which was generated from a first image of the eye 1, as well as a further histogram of oriented gradients 6b, which is e.g. generated from a second image of the eye 1. The shapes of the histograms 6a and 6b are the same, but a shift or displacement α of the histogram 6b with respect to the histogram 6a occurs along the axis of direction. The displacement α is a measure for the angle of torsion, i.e. for the angle of rotation of the eye 1, which occurred between the two camera recordings.

Thereby an additional relative displacement of the recorded images does not affect the histogram. A different scaling has the effect that the corresponding histograms differ from each other by a constant factor. In this case the features i.e. the blood vessels in both images consist of a differing amount of pixels because of the different image size, which can be equalized or compensated with the help of a normalisation. However, if the two histograms cannot be transformed into each other, for example by correlations, it is not the same feature.

Figures 5A, 5B:
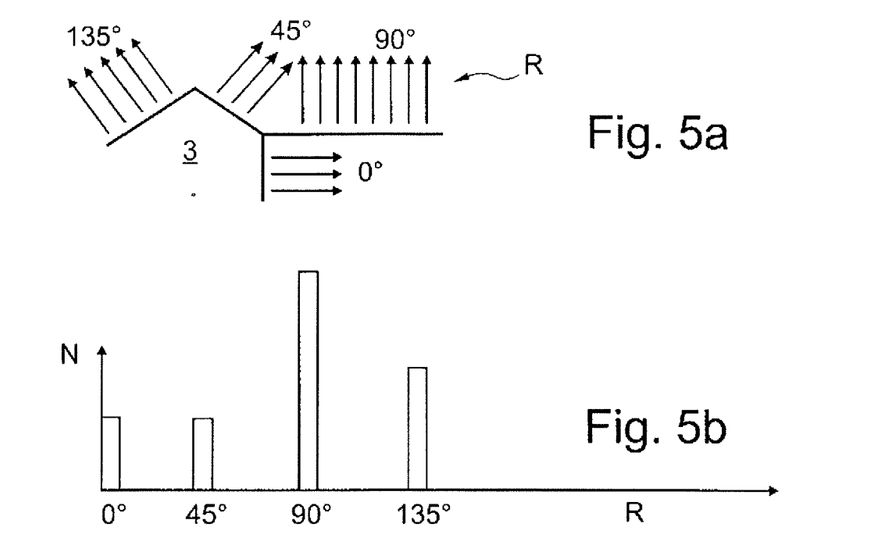
FIGS. 5a and 5b show a stylised blood vessel (FIG. 5a) and an appropriate histogram of the normal direction.

FIG. 5a shows a stylized blood vessel 3 in a first position with the corresponding gradient or normal directions R. In this example, a relatively large part of the blood vessel has a normal direction R of 90 degrees. Two relatively short sections of the blood vessel have a normal direction R of zero degrees respectively 135 degrees, and another section has a normal direction R of 135 degrees. FIG. 5b shows the corresponding histogram of the gradient- or normal directions R.

Figure 6A:
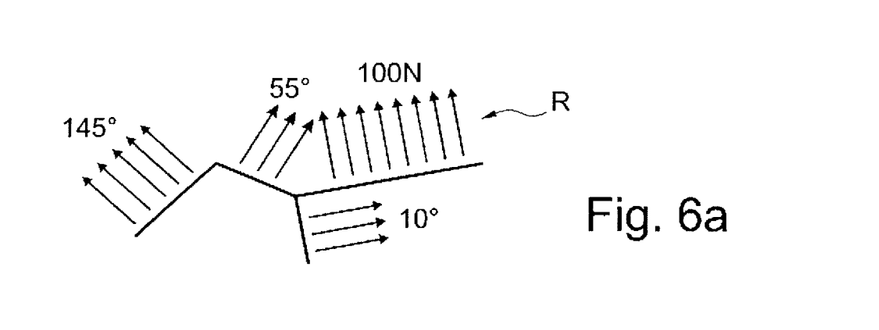
FIGS. 6a and 6b show the stylised blood vessel of FIG. 5a with the corresponding histogram of the normal direction, wherein the blood vessel is rotated by 10 degrees.
Figure 6B:
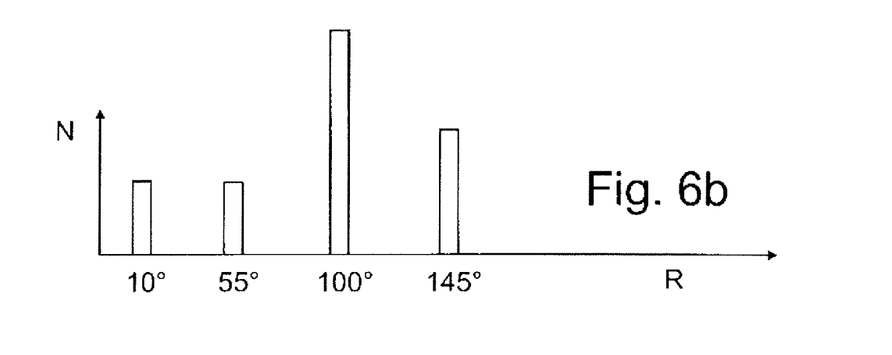

The FIG. 6a shows the blood vessel 3 with its gradient or normal directions R in a second position, in which it is rotated by ten degrees relative to the position shown in FIG. 5a. The related histogram which is shown in FIG. 6b shows normal directions of ten degrees, 55 degrees 100 degrees and 145 degrees.

Figure 7:
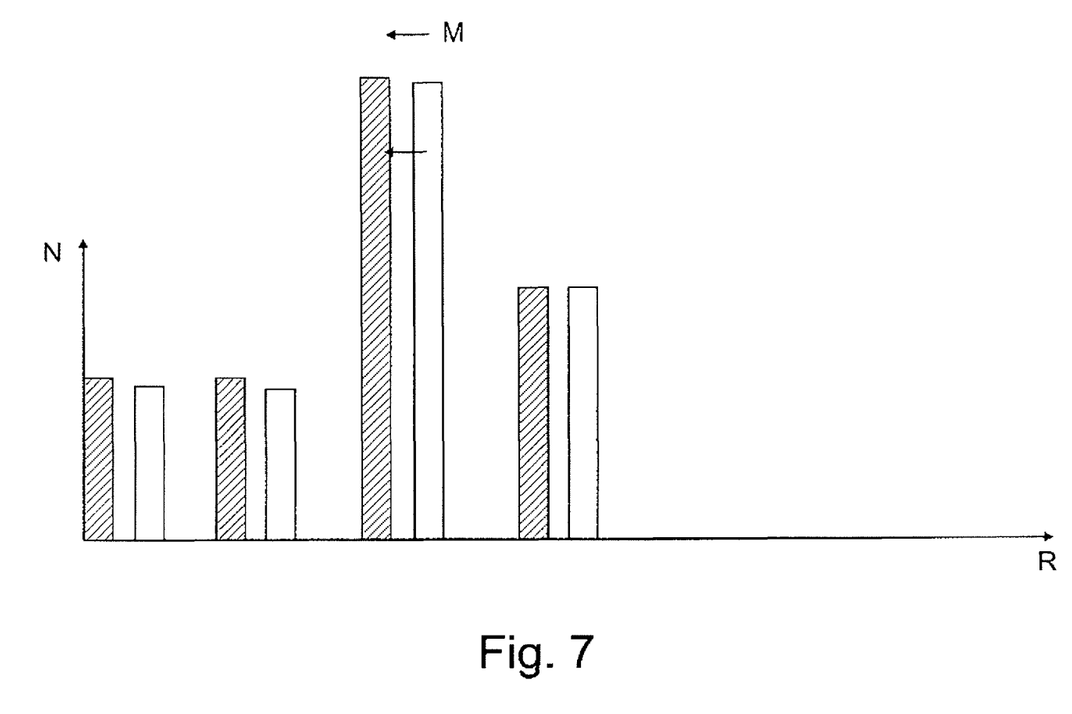
FIG. 7 shows the histograms of FIG. 5b and FIG. 6b for the determination of the torsion of the eye.

FIG. 7 illustrates schematically the matching process, with which the torsion angle between the two positions illustrated in FIGS. 5a and 6a is determined. The matching consists of bringing the histograms of FIGS. 5b and 6b through a one dimensional shift M into best possible mutual coverage. The torsion of the eye results from the shift.

Figure 8:
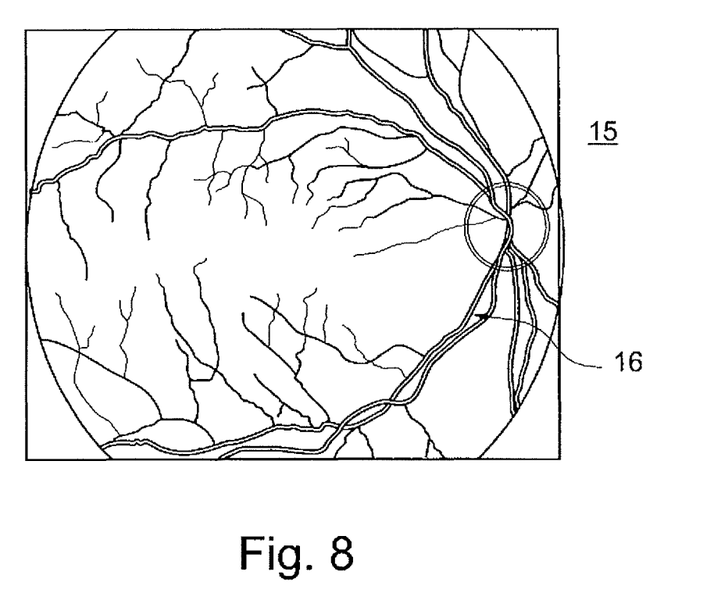
FIG. 8 shows an illustration of an eyeground or fundus with blood vessels.

FIG. 8 shows a recording of the eyeground or fundus 15. As an example of distinctive structures, blood vessels 16 are visible, which are identified according to a further embodiment of the invention in the image data as a characteristic feature, in order to create therefrom the direction histograms as described above, and to determine from the direction histograms the torsion angle of the eye.

Figure 9:
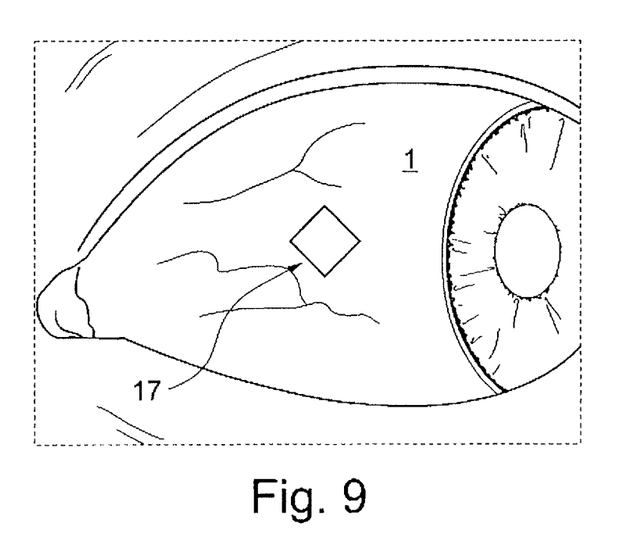
FIG. 9 shows an image of an eye with an artificially applied marker.

FIG. 9 shows another exemplary embodiment of the invention, where an artificially applied marker 17 on the sclera and/or on the cornea of the eye 1 is used as a characteristic feature for determining the torsion of the eye.

The invention claimed is:

1. A method for determining the eye torsion, comprising the steps:
    capturing at least two images of an eye and generating image data;
    identifying at least one characteristic feature of the eye from the image data;
    creating a histogram of the directions of the feature in both images;
    comparing the respective direction histogram of the feature in both captured images to each other; and
    determining a displacement α of the directions R in the direction histograms,
        wherein the method further includes using the direction histogram of the feature in both images to determine the rotation of the eye around its viewing direction, and the displacement α is used as a measure for the angle of rotation of the eye around its viewing direction, and
        wherein the histograms of the feature in both images are matched by a one dimensional shift M into best mutual coverage, where torsion of the eye is determined from the shift M.

2. The method of claim 1, wherein the direction histogram is a histogram of the gradient or tangential directions or of shifted directions of the feature.

3. The method of claim 1 wherein the characteristic feature is a blood vessel or a group of blood vessels.

4. The method of claim 1, wherein the method further comprises respectively calculating, in both images, one histogram of oriented gradients of a variety of blood vessels, where the angle of torsion of the eye is determined from their shift.

5. The method of claim 1, wherein the method further comprises dividing the at least two images into portions, and calculating a histogram of oriented gradients in each portion and using such for the comparison.

6. The method of claim 1, wherein the shapes of the direction histograms are compared, wherein for direction histograms of the same shape the displacement on the direction axis of the histogram is determined.

7. A computer program comprising a computer program code, which is designed for performing the method according to claim 1 with an image processing unit connected to a camera device.

8. The method of claim 1, wherein:
the direction histogram shows the frequency of occurrence of the directions of the feature in the image.

9. The method of claim 1, wherein:
the direction histogram is a histogram of a plurality of directions of the feature.

10. A device, wherein the device is configured to determine eye torsion, wherein the device includes:
    a camera for capturing at least two images of the eye and for generating image data; and
    an image processing unit for identifying at least one characteristic feature of the eye from the image data and for generating a direction histogram of the feature in both images;
    wherein the image processing unit is configured to compare the direction histograms of the feature and determines the angle of the torsion of the eye from a shift α of the directions in the direction histograms, wherein
    the device is configured to match the histograms of the feature in both images by a one dimensional shift M into best mutual coverage, where torsion of the eye is determined from the shift M.

11. A method for determining the eye torsion, comprising:
    (a) capturing a first image and a second image of an eye, and generating image data of the first image and the second image;
    (b) identifying at least one characteristic feature of the eye from the image data of the first image and the second image;
    (c) creating a histogram of the directions of the feature in each of the first and the second image as a direction histogram;
    (d) comparing the created direction histogram of the feature in the first image with the direction histogram of the feature in the second image; and
    (e) determining a displacement α of the directions in the direction histogram of the feature in the second image with respect to the directions in the direction histogram of the feature in the first image, wherein
    the direction histogram of the feature in the first image and in the second image is used for determining the rotation of the eye around its viewing direction,
    the displacement α is used as a measure for the angle of rotation of the eye around its viewing direction, and
    the histograms of the feature in both images are matched by a one dimensional shift M into best mutual coverage, where torsion of the eye is determined from the shift M.

12. The method of claim 11, wherein:
the directions in the direction histogram represent the gradient or normal directions of the feature or the tangential directions of the feature.

13. The method of claim 11, wherein:
the direction histogram shows the frequency of occurrence of the directions of the feature in the image.

14. The method of claim 11, further comprising:
determining the angle of torsion of the eye from the amount of a shift of the directions of the feature in the direction histogram.

15. The method of claim 11, further comprising:
comparing the shape of the direction histograms of the feature in both images.

* * * * *